United States Patent [19]

Zaromb et al.

[11] Patent Number: 4,888,295
[45] Date of Patent: Dec. 19, 1989

[54] PORTABLE SYSTEM AND METHOD COMBINING CHROMATOGRAPHY AND ARRAY OF ELECTROCHEMICAL SENSORS

[75] Inventors: Solomon Zaromb, Hinsdale; Joseph R. Stetter, Naperville, both of Ill.

[73] Assignee: The United States of America as represented by the United States Department of Energy, Washington, D.C.

[21] Appl. No.: 881,310

[22] Filed: Jul. 2, 1986

Related U.S. Application Data

[63] Continuation-in-part of Ser. No. 585,699, Mar. 2, 1984, Pat. No. 4,670,405.

[51] Int. Cl.$^4$ ............................................. G01N 30/78
[52] U.S. Cl. ............................... 436/161; 73/61.1 C; 73/23.1; 422/70; 422/89; 422/98; 436/175; 436/177; 436/151
[58] Field of Search ............................ 73/61.1 C, 23.1; 422/70, 89, 98; 436/161, 175, 177, 151; 364/496, 497, 498

[56] References Cited

U.S. PATENT DOCUMENTS

| | | |
|---|---|---|
| 3,352,643 | 11/1967 | Ando et al. . |
| 3,653,840 | 4/1972 | Silas . |
| 3,706,381 | 12/1972 | Joynes et al. . |
| 3,902,848 | 9/1975 | Juvet, Jr. et al. . |
| 3,961,248 | 6/1976 | Kawamura ........................ 422/98 X |
| 4,059,406 | 11/1977 | Fleet . |
| 4,181,853 | 1/1980 | Abu-Shumays et al. ........ 436/161 X |
| 4,383,433 | 5/1983 | Stacy .................................... 73/23.1 |
| 4,404,065 | 9/1983 | Matson . |
| 4,431,919 | 2/1984 | Kostlin et al. . |
| 4,440,726 | 4/1984 | Coulson . |
| 4,496,454 | 1/1985 | Berger . |
| 4,511,659 | 4/1985 | Matson . |
| 4,540,548 | 9/1985 | Imai et al. ........................ 422/70 X |
| 4,542,640 | 9/1985 | Clifford .............................. 422/98 X |
| 4,549,965 | 10/1985 | Davis ............................. 436/161 X |
| 4,552,013 | 11/1985 | Matson . |

FOREIGN PATENT DOCUMENTS

| | | | |
|---|---|---|---|
| 57-135355 | 8/1982 | Japan ................................... 436/161 |
| 903765 | 2/1982 | U.S.S.R. ............................... 436/161 |

*Primary Examiner*—Barry S. Richman
*Assistant Examiner*—Timothy M. McMahon
*Attorney, Agent, or Firm*—Hugh G. Glenn; Robert J. Fisher; William R. Moser

[57] ABSTRACT

A portable system for analyzing a fluid sample includes a small, portable, low-pressure and low-power chromatographic analyzer and a chemical parameter spectrometry monitor including an array of sensors for detecting, identifying and measuring the concentrations of a variety of components in the eluent from the chromatographic analyzer. The monitor includes one or more operating condition controllers which may be used to change one or more of the operating conditions during exposure of the sensors to the eluent from the chromatography analyzer to form a response pattern which is then compared with a library of previously established patterns. Gas and liquid chromatographic embodiments are disclosed. In the gas embodiment, the operating condition controllers include heated filaments which may convert electrochemically inactive components to electrochemically active products. In the liquid chromatography embodiment, low-power, liquid-phase equivalents of heated filaments are used with appropriate sensors. The library response patterns may be divided into subsets and the formed pattern may be assigned for comparison only with the patterns of a particular subset.

20 Claims, 9 Drawing Sheets

PORTABLE SYSTEM AND METHOD COMBINING CHROMATOGRAPHY AND ARRAY OF ELECTROCHEMICAL SENSORS

CONTRACTUAL ORIGIN OF THE INVENTION

The United States Government has rights in this invention pursuant to Contract No. W-31-109-ENG-38 between the U.S. Department of Energy and the University of Chicago representing Argonne National Laboratory.

CROSS-REFERENCE TO RELATED APPLICATION

This application is a continuation-in-part of U.S. application Ser. No. 585,699 now U.S. Pat. No. 4,670,405, filed Mar. 2, 1984 by Joseph R. Stetter, Solomon Zaromb and William R. Penrose, and entitled "Sensor Array for Toxic Gas Detection".

BACKGROUND OF THE INVENTION

The present invention relates to analytical instruments for detecting hazardous materials, and in particular to portable instruments.

This invention relates to analytical devices and, more particularly, to devices for detecting the presence of at least one pollutant or other hazardous component in a fluid sample. Such devices are needed, for example, in hazardous waste activities, such as site surveys to determine the presence of pollutants, location and identification of contamination, as well as certification of the absence of contamination (e.g. during transport and storage of wastes), monitoring of waste streams, and maintenance and operation of facilities. Hazardous wastes may include a large number of different materials. Detection devices are known for detecting and measuring one or a few selected pollutants, but they are not designed to identify unknown pollutants. When a gas for analysis may contain an unknown pollutant, it is usually necessary to obtain a sample of the gas and send it to a laboratory for a remote analysis, a costly and time-consuming operation.

In the aforementioned copending U.S. application Ser. No. 585,699, there is disclosed a low-power, portable, analytical device for identifying hazardous components in a gas, such as air, through the use an array of small sensors, such as electrochemical sensors, to provide a pattern of responses which is compared to a library of previously established response patterns to provide an identification of a component of the gas. The array also includes at least one heating filament capable of producing one or more derivatives by oxidation or pyrolysis of the component, so that the device is usable for detecting electrochemically inactive components. In addition, the responses from the sensors may be varied by changes in one or more of the operational conditions, such as voltage, temperature, sample flow rate, or diversion of the sample through a selective chemical filter and the like, so that the number of different responses is greater than the number of sensors and the number of detectable components in the gas. Analysis of the responses also provides data on the concentration levels of the hazardous component or components. That device has afforded adequate sensitivity for detecting hazardous components in concentrations as small as 1 ppm (parts per million).

But it is frequently necessary to detect certain hazardous components, such as certain organic chemicals, in trace amounts down to levels of one ppb (parts per billion) or less in complex mixtures. Techniques exist for analyzing such organic chemicals, but they are expensive and time consuming and require transport of samples to the laboratory. For example, gas chromatographic methods have been utilized, but it has been found that high column temperatures and, thus, large power outputs are required for efficient separation of organic chemicals such as primary aromatic amines. Furthermore, the primary aromatic amines must be absorbed or condensed from the air samples to improve the sensitivity of the assay. Once the sample is absorbed or condensed, it has to be flash-volatilized into the chromatography column. This procedure also consumes large amounts of energy. The large power requirements for such gas chromatography are not feasible in a portable instrument.

It has been suggested that a liquid chromatograph may be combined with electrochemical detectors, such an approach being disclosed in U.S. Pat. No. 4,511,659. But that arrangement uses standard analytical chromatography techniques utilizing large chromatographic columns, typically well in excess of 10 cm. in length, the system not being suitable for use in a portable instrument.

Small (3 cm.) chromatographic columns are known, but they are typically used for "cleanup" operations, serving as disposable pre-filters for separating certain chemical components prior to passing them through a large analytical chromatographic instrument. Such small devices have not heretofore been recognized as being capable of providing the high resolution necessary for an analytical instrument. Rather, it has been recognized that to increase resolution it is generally necessary to provide longer chromatographic columns, higher pressures and higher energy consumption, all of which detract from portability and field operation.

SUMMARY OF THE INVENTION

It is a general object of the invention to provide an improved analytical instrument which avoids the disadvantages of prior instruments while affording additional structural and operating advantages.

An important feature of the invention is the provision of an analytical system that is portable and is yet capable of analyzing a large variety of hazardous contaminants that may be encountered in trace quantities.

In connection with the foregoing feature, it is another feature of the invention to provide a system of the type set forth which is compact and characterized by low power consumption.

Still another feature of the invention is the provision of a system concept of the type set forth which is adaptable for analyzing components in either gas or liquid phase.

Still another feature of the invention is the provision of a system of the type set forth which is capable of detecting and measuring the concentration of electrochemically inactive components in a mixture.

In connection with the foregoing features, it is another feature to provide a system of the type set forth which is flexible enough to meet the needs of both fixed-site and portable instruments.

Still another feature of the invention is the provision of an analytical method in which the system of the type set forth may be used.

These and other features of the invention are attained by providing a portable system for analyzing a fluid sample including mixtures of components, comprising: portable chromatographic apparatus for achieving time spaced separation of components of the sample, the chromatographic apparatus including a chromatographic column and having an inlet and an outlet, means for introducing a carrier fluid to the inlet of the column, and means for introducing a fluid sample to the inlet of the column; portable detection means communicating with the outlet of the column for identifying and estimating the concentration of the components eluting from the column, the detection means including an array of sensors, the array including plural sensors, preferably electrochemical sensors, having differing responses to one of the eluted components or a derivative thereof dependent on the chemical interaction of the component or a derivative thereof with each of the sensors and also dependent on an operational condition of at least one of the sensors, and conditioning means for controlling the operational condition; means for forming a response pattern from the array of sensors upon exposure to the component; means for providing a plurality of previously established response patterns including a previously established response pattern for identifying the component; and means for comparing the formed response pattern with at least one previously established response pattern to identify the component.

Additional objects, advantages and novel features of the invention will be set forth in part in the description which follows, and in part will become apparent to those skilled in the art upon examination of the following or may be learned by practice of the invention. The object and advantages of the invention may be realized and attained by means of the instrumentalities and combinations particularly pointed out in the appended claims.

BRIEF DESCRIPTION OF THE DRAWINGS

For the purpose of facilitating an understanding of the invention, there are illustrated in the accompanying drawings preferred embodiments thereof, from an inspection of which, when considered in connection with the following description, the invention, its construction and operation, and many of its advantages should be readily understood and appreciated.

DESCRIPTION OF THE PREFERRED EMBODIMENTS

The present invention is directed to a method and associated system for analyzing samples to detect hazardous components which may be present in only trace amounts and in the presence of much higher concentrations of potential interfering components. The invention is particularly directed to a portable system which is usable in the field for detecting one or more hazardous components in a gaseous or liquid medium, as well as being useful in fixed-site monitoring applications. A fundamental aspect of the invention is the combination of a portable chromatographic analyzer with a portable CPS (chemical parameter spectrometry) detector comprising an array of sensors, in combination with a conditioning means for controlling operational conditions of the sensors.

Figure 9:
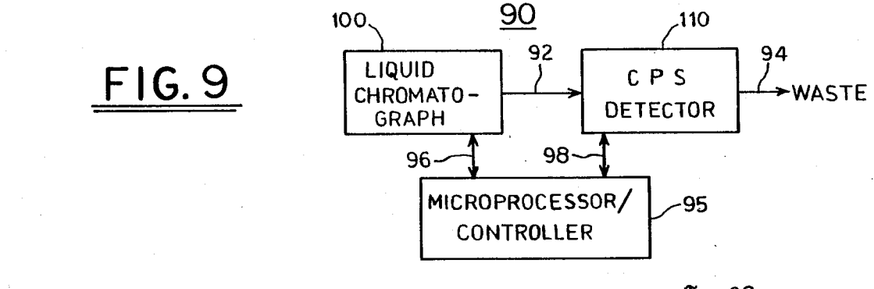
FIG. 9 is a block diagram of a system, constructed in accordance with and embodying the features of a first embodiment of the present invention for operating in the liquid phase and combining a liquid chromatograph with a detector array analogous to those disclosed in FIGS. 5 and 6.
Figure 12:
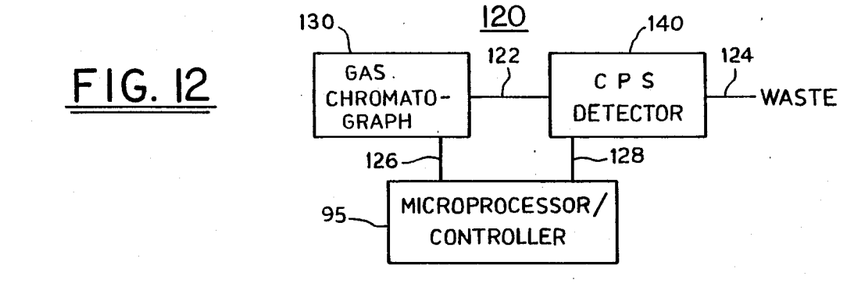
FIG. 12 is a block diagram, similar to FIG. 9, illustrating a system in accordance with a second embodiment of the present invention for operation in the gas phase.

FIGS. 9 and 12, respectively, illustrate liquid and gas phase embodiments of the invention. Thus, in FIG. 9 there is illustrated a system 90 including a liquid chromatographic analyzer 100, the eluent from which is fed through a CPS detector 110, both the chromatographic analyzer 100 and the CPS detector 110 operating under control of a microprocessor/controller 95. In FIG. 12, there is disclosed a gas system 120 in which the microprocessor/controller 95 controls a gas chromatographic analyzer 130 and a CPS detector 140. The gas CPS detector 140 is very similar to that disclosed in the aforementioned copending U.S. application Ser. No. 585,699, while the CPS detector 110 is a liquid phase analog of the gas detector 140.

The CPS detector of copending application Ser. No. 585,699, is particularly useful in detecting, identifying and determining the concentrations of a large number of hazardous components which may occur in mixtures including several such components. Representative hazardous components with which that CPS detector provides useful results include acrylonitrile, ammonia, benzene, carbon monoxide, carbon tetrachloride, chlorine, chloroform, cyclohexane, ethyl acrylate, formaldehyde, hydrogen sulfide, nitric oxide, nitrogen dioxide, nitromethane, pyridine, sulfur dioxide, sulfuryl fluoride, tetrahydrofuran, toluene, and vinyl acetate.

The TWA (time-weighted average) toxic level of the above hazardous components vary from about 1 ppm for chlorine or formaldehyde to about 300 ppm for cyclohexane. However, for short term exposure, it may be more important to detect and identify one or more of these components at levels in the order of about 2 to 400 (usually 10 to 50) ppm. In the CPS detector, these components are detected by their chemical interaction or that of their derivatives with the sensors in the array. Usually, the component has a chemically active group or groups or may be oxidized or reduced to form one or more derivatives having an active group or groups such as carbon monoxide, nitrogen dioxide, etc.

In the CPS detector, each of the sensors in an array is provided with a housing or other gas containment system forming a sample chamber with the combination forming a sensing means. Means are provided for introducing a gas sample to the sensing means which typically may be the sensing electrode of an electrochemical, especially of an amperometric, gas sensor. The sensors include at least two, and preferably at least 3–4, sensors having different electrical responses to a component or its derivative to provide a plurality of different responses. Usually, the responses differ between sensors for the same component and between components for the same sensor.

As an illustration of the operation of an instrument embodying such a CPS detector, the instrument can be set to perform one of two principal functions—monitoring or identification. When monitoring for the presence of any unknown air contaminant, the sensor array is connected directly to a sampling probe, and a signal from any of the sensors indicates the presence of a possibly hazardous component near the probe intake. To identify the detected component, a sample is first drawn from the probe intake into a 1-liter (L) sampling bag. The collected sample is then drawn through the sensor array at a rate of about 0.01–0.1 L per minute, and the sensors are switched into four differently selective modes at appropriate intervals (usually 40 seconds/interval). The responses of each sensor at the end of each interval are recorded in one of 16 independent data channels, and the relative magnitudes of these response signals provide the information needed to identify the particular component giving rise to the observed signals. The microprocessor-controller identifies a compound based on the recorded data and then sets the sensor array for maximum sensitivity to that compound in the monitoring mode. The number of sensors and time required may be varied according to the complexity of the analyte. Simpler mixtures may require smaller arrays and fewer modes of operation than the more complex analytes. It can also set the alarm to correspond to an appropriate level associated with the short term exposure limit (STEL) or immediate danger to life and health (IDLH) concentration of the identified compound.

The sensor array may comprise electrochemical, catalytic or semiconductor-type sensors, or combinations of these and other types of portable lower-power gas sensors, and preferably will be primarily electrochemical. The sensor array may also include one or more heating filaments having exposed catalytic surfaces. Suitable types of electrochemical sensors include amperometric sensors having gold or platinum sensing electrodes supported on either an ion-exchange, e.g., polyfluorosulfonic acid, membrane, which also serves as the sensor electrolyte, or on a gas-permeable electrolyte-impermeable porous polytetrafluoroethylene membrane, with the sensor electrolyte being either a strong acid, such as $H_2SO_4$ or $H_3PO_4$, or a strong base, such as KOH, in aqueous solution. Sensors using other metal and non-metal electrodes in aqueous or non-aqueous solutions may also be used. The array may also include one or more heating filaments containing catalytic material, such as platinum, palladium, iridium, rhodium or gold, and preferably two separate filaments, e.g., one of platinum and one of rhodium. These filaments may function to provide different degrees of oxidation of the component and also to act as sensors whose electrical current will vary with the concentration of the component.

Figure 5:
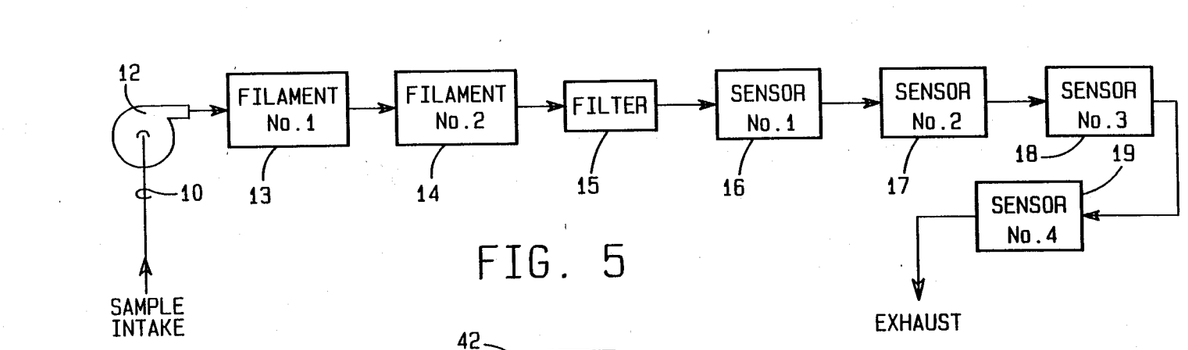
FIG. 5 is a block diagram of one embodiment of the invention with a sensor array having sample chambers connected in series.
Figure 6:
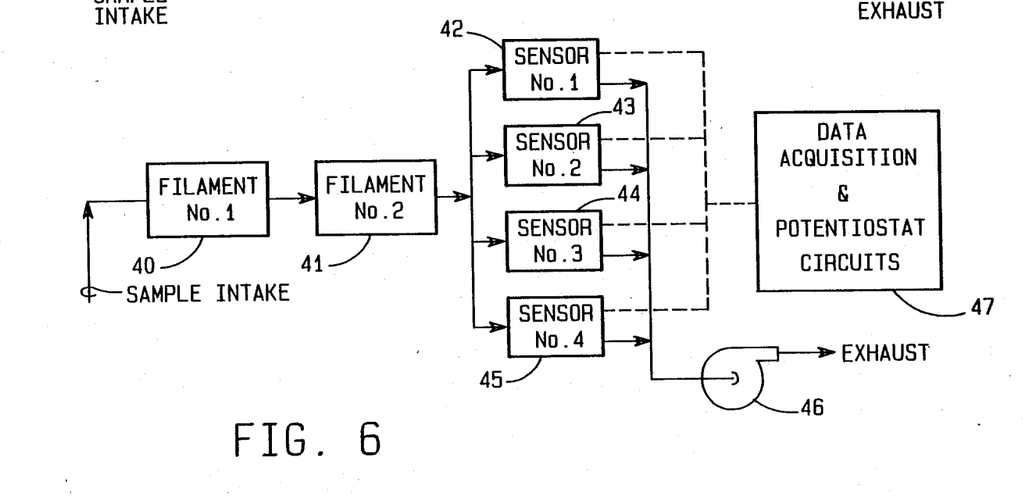
FIG. 6 is a block diagram of a second embodiment of the invention with a sensor array having sample chambers connected in parallel.

When a gas sample is caused to flow past the filaments before being exposed to a sensor array, as indicated in either of FIGS. 5 or 6, then the partial oxidation or pyrolysis of a component caused by heating one of the filaments becomes equivalent to converting the sensor array to a differently selective operating mode.

An alternative or complementary way of increasing the number of differently selective operating modes, and thereby achieving improved selectivity, is to divert the sample past one or more selective chemical filters (e.g., cartridges containing materials having strong chemical affinity for certain compounds) by means of electronically controlled solenoid valves (not shown). Such filters may comprise activated charcoal or other adsorbents, to remove organic vapors, or chemical reagents such as triethanolamine on a support to remove nitrogen dioxide. By comparing the responses of the sensor array to a sample passed through no chemical filter with the responses to the same sample passed through one or more different chemical filters, identification of the tested compound or compounds may be greatly facilitated.

In any case, for a number S of differently selective sensors in an array and a number M of differently selective operating modes, the maximum number of independent parameters (or data channels) P that can be obtained upon exposure to a test sample is given by the product MS, i.e., $P = MS$. The larger the value of P, the larger the number of different components that can be identified by a sensor array.

Figure 1A:
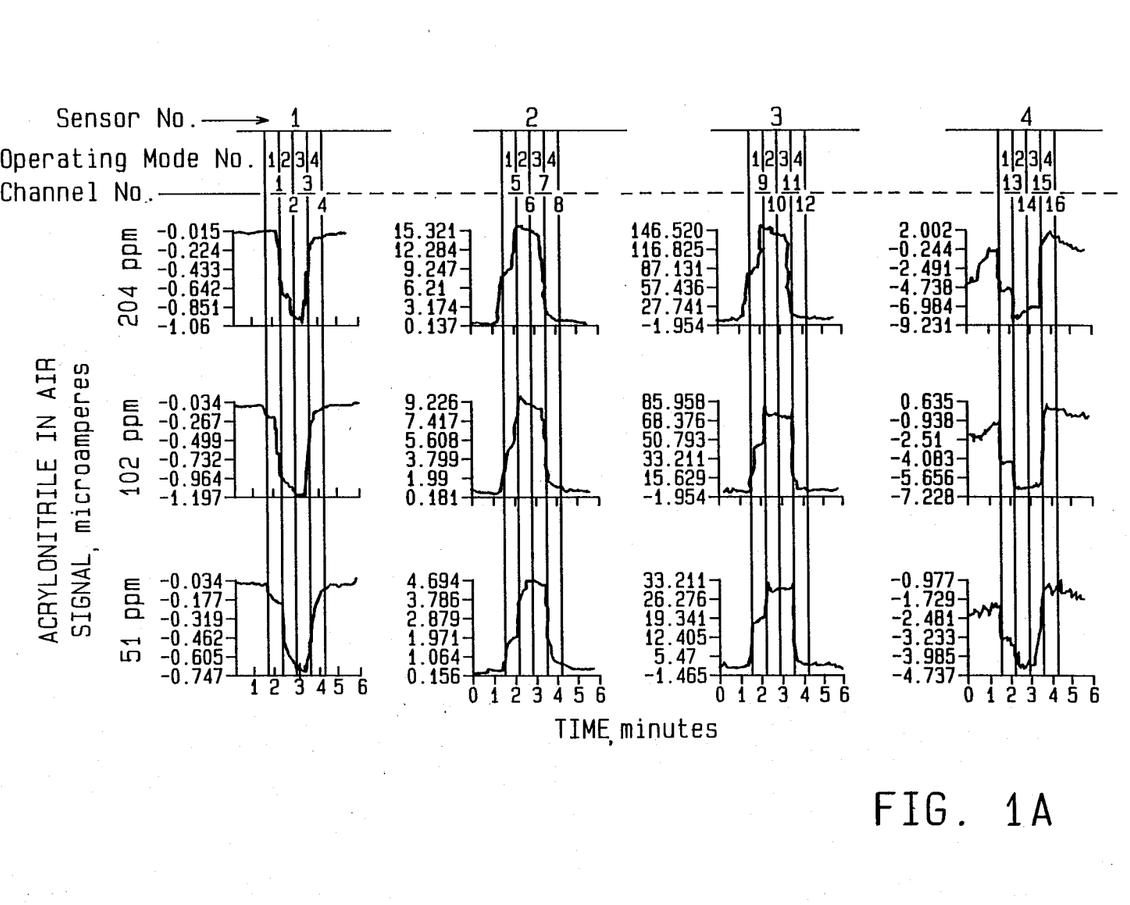
FIGS. 1A and B is a series of graphs showing the response patterns for acrylonitrile from an array of sensors including four electrochemical sensors.
Figure 1B:
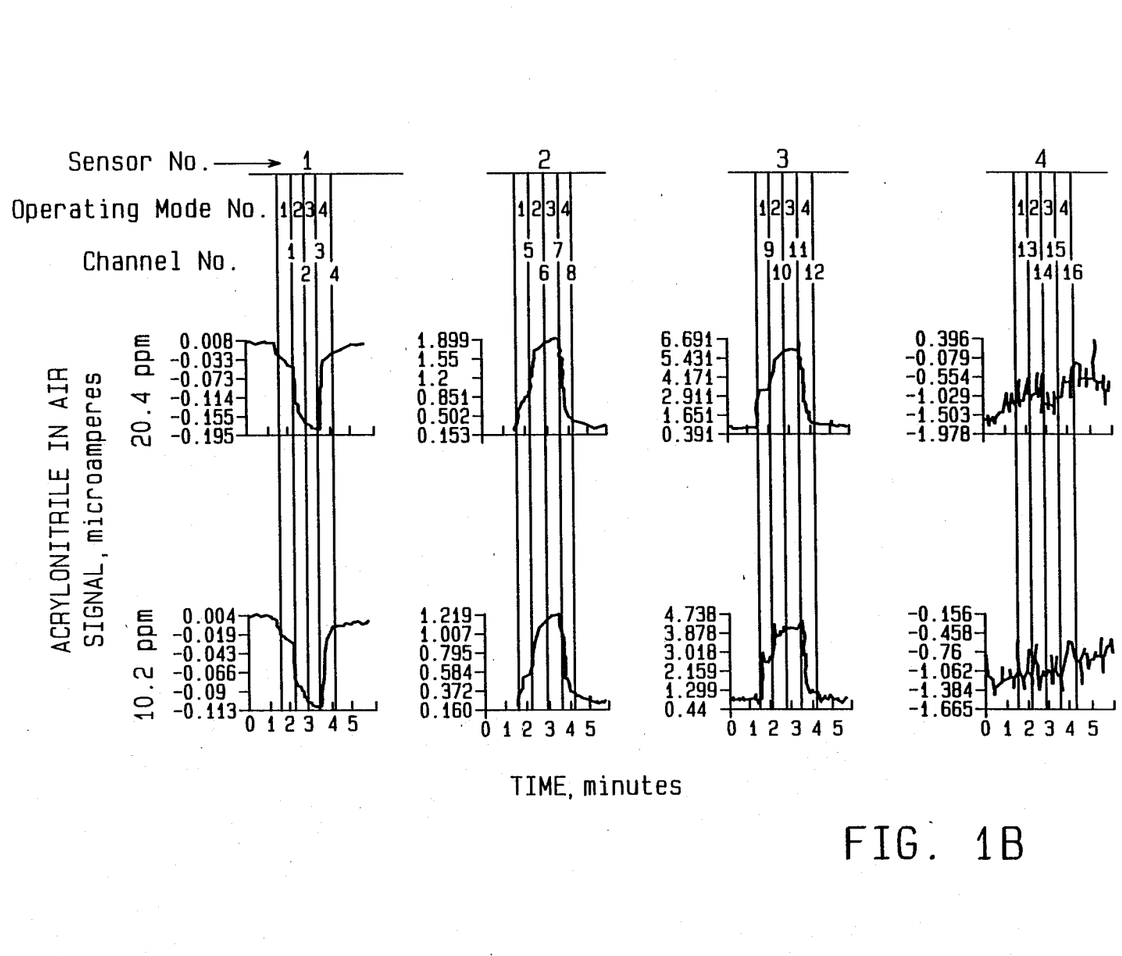
Figure 2:
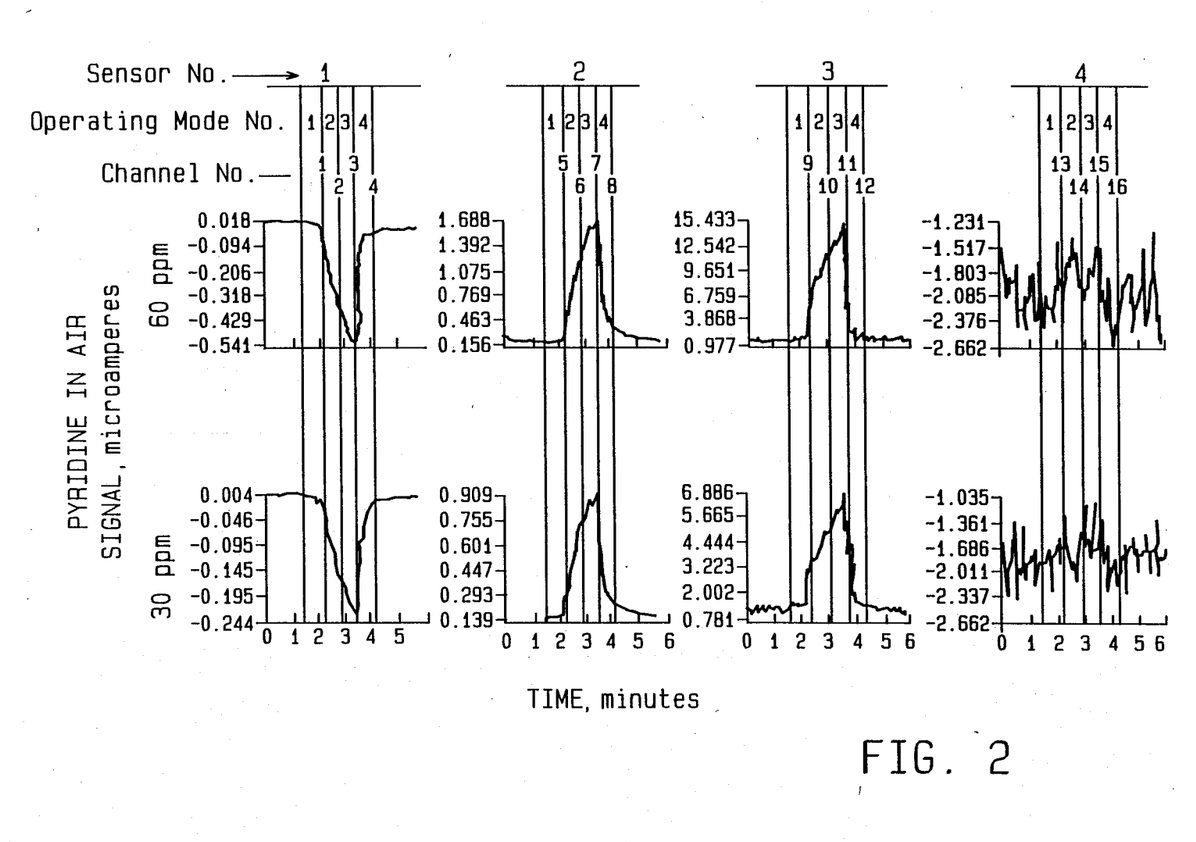
FIG. 2 is a series of graphs showing the response patterns to pyridine from an array of sensors including four electrochemical sensors.
Figure 3:
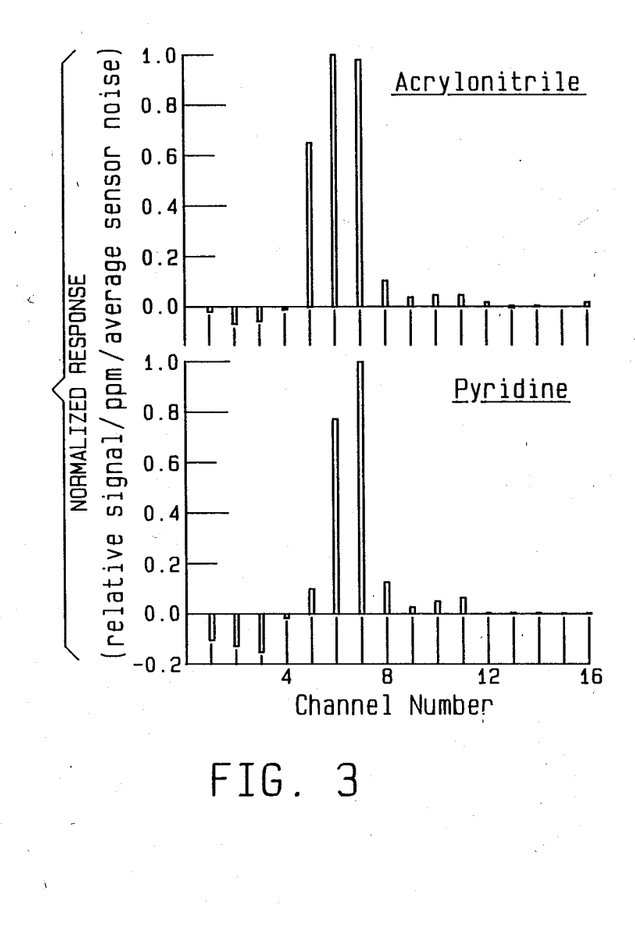
FIG. 3 is a pair of histograms of normalized responses of 16 channels to toxic vapors of acrylonitrile and pyridine.

As an illustration of the detection of hazardous components, FIGS. 1 and 2 provide data for acrylonitrile and pyridine, respectively. The array includes four different electrochemical toxic gas sensors—two with pure gold mesh sensing electrodes embedded in a polyfluorosulfonic acid ion-exchange membrane, one of the electrodes being kept at a potential of 1.0 volt and one at a potential of 1.4 volt versus RHE (the reversible hydrogen electrode), one with a similar electrode made of platinized platinum mesh and kept at 1.3 volt versus RHE and one with a sensing electrode of platinum black bonded to a porous tetrafluoroethylene membrane, immersed in an approximately 25–30 wt. % sulfuric acid electrolyte, and potentiostated at 1.1 volt versus RHE—and two heated noble metal filaments—one of platinum and one of rhodium—that function to partially oxidize or pyrolyze many compounds in air. The four sensors may be rapidly switched to one of the following four operating modes: (a) platinum filament heated to about 850° C.; (b) filament heated to about 900° C.; (c) rhodium filament heated to about 1000° C.; and (d) both filaments off. In this arrangement, four modes and four sensors provide a total of 16 independent data channels as illustrated in FIGS. 1 and 3. In FIG. 1, each of four sensors was exposed to predetermined amounts of acrylonitrile in air and was operating in each of the foregoing four modes. As indicated by the data, each sensor has a different electrical response pattern to exposure to acrylonitrile with the response changing with concentration. A similar result is shown in FIG. 2 for pyridine. The responses in FIGS. 1 and 2, when normalized as set forth in FIG. 3, exhibit different histogram patterns for different compounds, thereby permitting identification of a sampled compound. Moreover, as illustrated in FIG. 4, the magnitude or amplitude of the strongest channels in FIG. 3 may be used as an indication of the concentration of the identified hazardous component.

Figure 4:
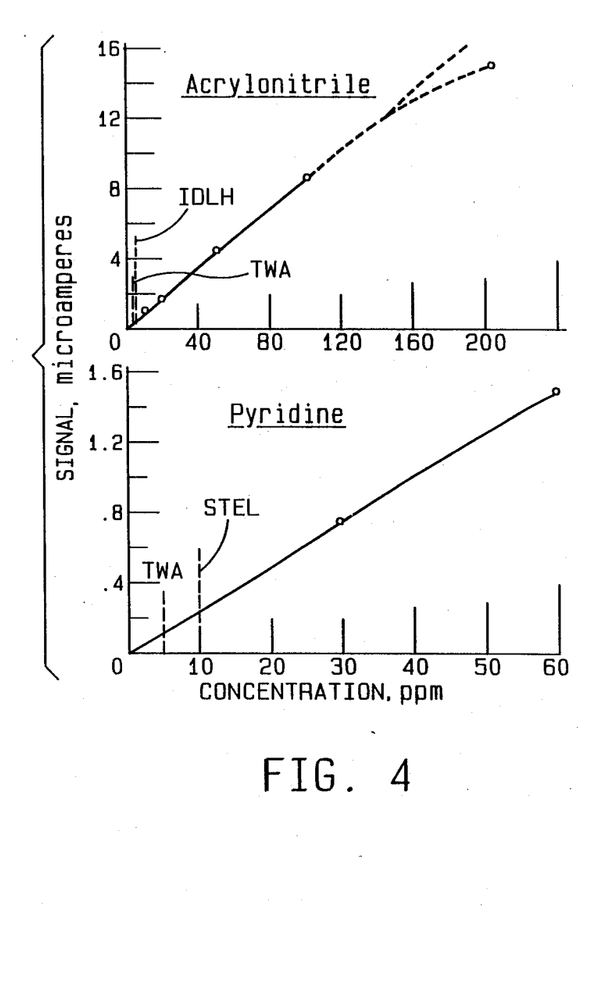
FIG. 4 is a pair of graphs showing the proportionality of the response signals in the strongest channels of FIG. 3 to the sampled toxic vapor concentration.

Further with respect to FIG. 4, the data also shown the TWA threshold exposure level and the STEL or IDLH concentrations of the two components.

The device may function either to monitor the level of a component or to identify unknown components. FIG. 3 shows that channel 6 provides the strongest signal for acrylonitrile while channel 7 provides the strongest signal for pyridine. Therefore, the sensor array as a monitor will be tuned to channel 6 after having identified acrylonitrile or to channel 7 after having identified pyridine.

Programming means are provided to form sensor responses into a response pattern. As illustrated in FIG. 3, the responses may be positive, at or about zero, or negative. These responses collectively form one or more response patterns which serve to identify the component.

Advantageously, the programming means include means for comparing the formed response pattern with one or more standard or previously established patterns, each being characteristic of a particular component or type of component. Preferably, the programming means also include a memory which provides the standard patterns for the comparison.

Prior to the comparison, the initial or first response pattern is converted to a second pattern in which noise and blank readings are removed. As an illustration, the responses in FIG. 3 are obtained by dividing the responses initially obtained by the corresponding toxic gas concentration and also by the average noise of each sensor corresponding to a given channel. The values in each channel are then normalized by dividing them by the highest response in the 16-channel response pattern to provide FIG. 3.

In environments where the number of possible detectable components exceeds the number P of independent parameters or data channels, gas samples containing mixtures of more than one unknown detectable component may be resolved. To resolve such a mixture of unknown components in a gas sample, the programming means can first reject those candidate compounds whose response patterns call for significant signals in those channels in which the tested sample gave no significant response. In the examples of FIGS. 1-3, an insignificant response in Channel No. 1 (corresponding to Sensor No. 1 in Operating Mode No. 1) would exclude pyridine as a candidate compound, but would be compatible with the presence of acrylonitrile. This can be followed by additional prescreening steps. For instance, the programming means can then select those remaining candidate compounds whose response patterns exhibit strong responses in the same channels as in the actually observed response pattern. For instance, strong responses in Channel Nos. 5, 6 and 7 of FIG. 3, would point to acrylonitrile as a possible candidate compound. Finally, should this selection process yield more than one likely candidate compound, then the concentrations of each of these likely candidates may be estimated by solving several simultaneous algebraic equations (developed from an analysis of the standard response pattern) based on a comparison of the actual response pattern with the response patterns of the likely candidate compounds. All of these comparisons can be performed rapidly using a microprocessor built into the instrument.

FIG. 5 and 6 provide schematic sketches of sensor array arrangements. As illustrated in FIG. 5, the sample inlet 10 includes pump 12 to cause a flow of sample to filaments 13 and 14 which may be individually switched on or off or both on and off during the analysis. Filter 15 is provided to remove particulates. The resulting sample may be the initial component or its derivative or derivatives depending on whether filaments 13 and/or 14 are utilized. The resulting sample is then fed sequentially to sensors 16, 17, 18 and 19. These sensors are also arranged so that the first few sensors in the sequence interact with only minimal amounts of the sample without significantly altering the concentration introduced into the sample chambers of the subsequent sensors.

In FIG. 6, the sample is fed to filaments 40 and 41 and then to sensors 42, 43, 44 and 45 arranged in parallel. After interacting with these sensors, the sample is removed via pump 46. Data acquisition and potentiostat circuits 47 are provided to receive the responses and provide changes in the voltages of the sensors.

Figure 7A:
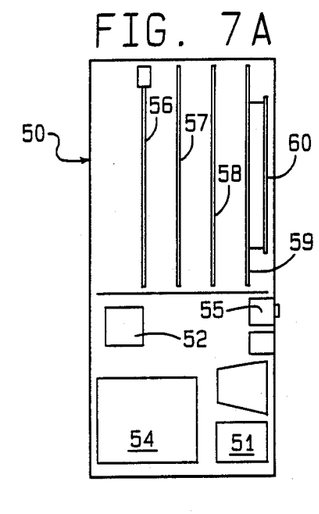
FIG. 7A represents a side view of a portable instrument embodying the invention.
Figure 7B:
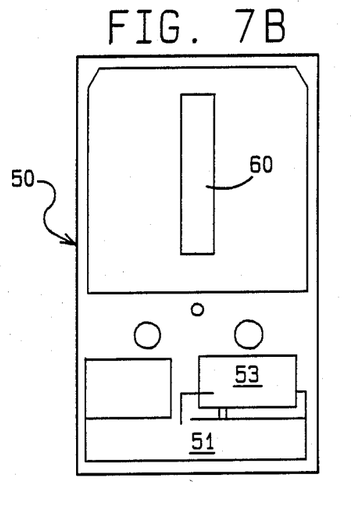
FIG. 7B represents a front view of the portable instrument of FIG. 7A.

FIG. 7A and 7B provides an arrangement of side and front views of a portable instrument. As illustrated, a housing 50 is provided which may be about 8 cm. by 28 cm. by 22 cm. Electrochemical cells 51 and filament 52 are provided as the array. Pump 53 acts to introduce the sample. Batteries 54 provide portable power. Filter 55 acts to remove particles. Four circuit boards are provided. Board 56 provides the CPU (central processing unit), board 57 provides the potentiometer and self-test circuits, board 58 provides the analog circuit, and board 59 provides power, alarm and display circuits. Display module 60 provides a display of data from each test.

Figure 8:
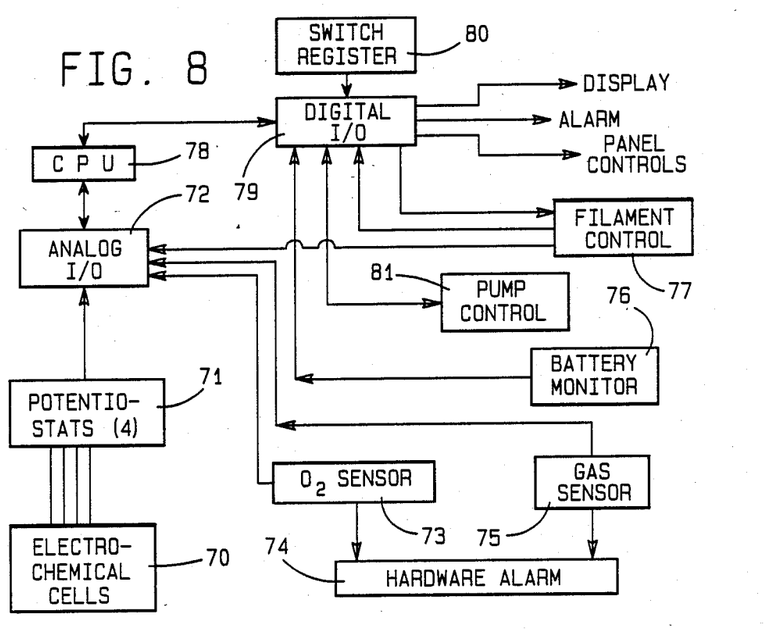
FIG. 8 is a block diagram of the data generating and processing systems associated with the invention.

FIG. 8 illustrates the interconnection of the parts of the device. Electrochemical cells 70 are controlled by potentiostats 71 with the responses from cells 70 being fed to an analog input/output 72 which also receives data and/or instructions from oxygen sensor 73, alarm 74, flammable gas sensor 75, filament control 77, and CPU 78. Digital input/output 79 also is operated by switch register 80, battery monitor 76, filament control 77, CPU 78 and pump control 81. Display and alarm signals are provided by digital input/output 79.

The device is provided with microprocessor programming means in which a master program is used to select any of a plurality of functional programs which in turn may utilize one or more of certain of the other functional programs and one or more utility programs. Selection of the functional program in the preferred embodiment is by the use of an appropriate key on the face of the housing. A display is provided to show the name of the component identified by the programming means in the test or the component being monitored.

In one preferred embodiment, the functional programs are named the Ident mode, the Select mode, the Universal mode, the Zero mode, the Calibrate mode, and the Test mode. All of these programs are operated using key strokes by the individual operators that activate the microprocessor to run the desired program. As illustrations of these modes, the following description is provided with the term "gas" intended to refer to the "component" being detected.

The Ident mode collects a set of data from an unknown gas (16 data points, 4 electrochemical cells in 4 modes), subtracts a set of zero data (the signals obtained from background air), multiplies by calibration data (obtained from a calibration gas to take into account the changing performance of cells, if any), and by treating the result as a 16-coordinate vector, compares the data to a series of pattern data sets stored in a library for various gases (the unknown gas data is normalized, and a euclidean distance calculation is performed between it and every pattern set). The gas having the pattern data which is the closest to the unknown is selected as the proper identification for the gas, and any pattern data sets having a distance from the unknown equal to or less than twice the minimum distance are selected as possible or incipient identifications. The concentration of the gas is calculated by multiplying the data from the strongest channel by a concentration coefficient stored in the pattern data library, and from the results of this calculation the percent IDLH level is also determined. All of this information is displayed, and alarms are set off at the 25% and 100% IDLH level (a beeping buzzer and flashing LEDs (light-emitting diodes) at 25% or greater, and a steady buzzer and LEDs at 100% and higher). Finally, the option is provided to the operator to review the information (gas identified, concentration, percent IDLH, number of incipient misidentification, and a list of incipient misidentifications) or to exit back to master program or a routine "Main" by pressing the proper key. Exiting back to Main shuts off any alarms.

The Select mode allows the operator to choose which of the gases in the pattern library to monitor. The gas is chosen by advancing forwards or backwards through the library, using the keyboard (only the name of the gas is displayed). When the proper gas is located, the operator can choose to either initiate the mode or exit back to MAIN. Once initiated, the device is operated only in the most sensitive mode, so that only four channels of data are taken. The euclidean distance is calculated based on only four channels to give a measure of how well the measured gas fits the pattern vector. This feature is intended to warn of mixtures of vapors or of mislabeling of chemicals. Select mode provides a measurement in a time appropriate for the mode (32 to 50 sec). The program may be interrupted after any cycle.

The Universal mode is to detect possible hazardous compounds prior to their identification. A Pt or Rh filament cycles on and off with 5–20-second duty cycles. The sensor responses are reported to the operator as a set of four arbitrary numbers; the alarm is triggered when any cell output exceeds a predetermined threshold.

The no-signal state of the device must be frequently measured. Upon entering the Zero mode, the 16 channels of information are acquired using the same routine (Volts) that is called by the Ident mode. Afterward, the 16-element vector is transferred to a special register. In subsequent measurements, this value is subtracted from all incoming data in the Ident, Select, or Universal modes.

Similarly, the aging of electrochemical cells and filaments is expected to cause gradual changes in responses over time. The Calibrate mode is designed to calculate a correction factor for each channel. A sample of a calibration gas such as sulfur dioxide is attached to the device. The data acquisition subroutine (Volts) is called. The resulting vector is compared to that stored in the pattern library, and the ratio is stored in a special register. Each subsequent measurement in the Ident or Select modes is corrected by this ratio. If Calib is not selected, a default vector is loaded into the calibrate register, representing the state of the cells at the time the library was compiled.

The Test mode gives access to the same monitor program that was used in program development on the device. The monitor program permits these functions.
 (a) Reading any portion of memory.
 (b) Changing values in RAM memory.
 (c) Resetting the instrument.
 (d) Calling certain subroutines used for device testing. For example, Control can be used to manually control pump speed and both filaments.

Test mode is not intended for routine operator use. If Test mode is inadvertently entered, two keystrokes will escape this mode.

Figure 10:
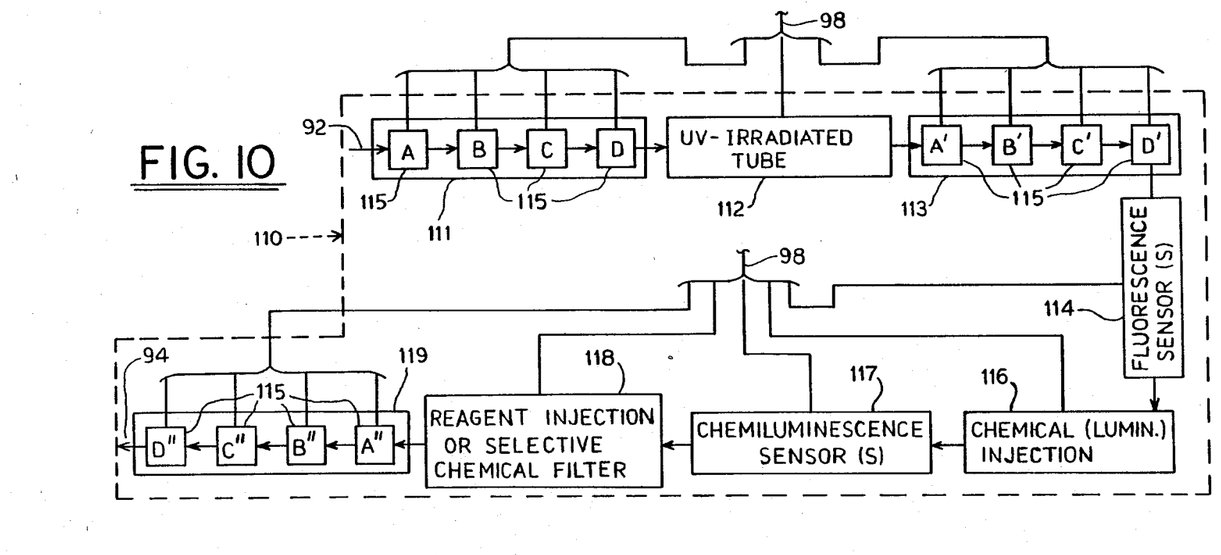
FIG. 10 is a more detailed block diagram of the detector utilized in the system of FIG. 9.
Figure 11:
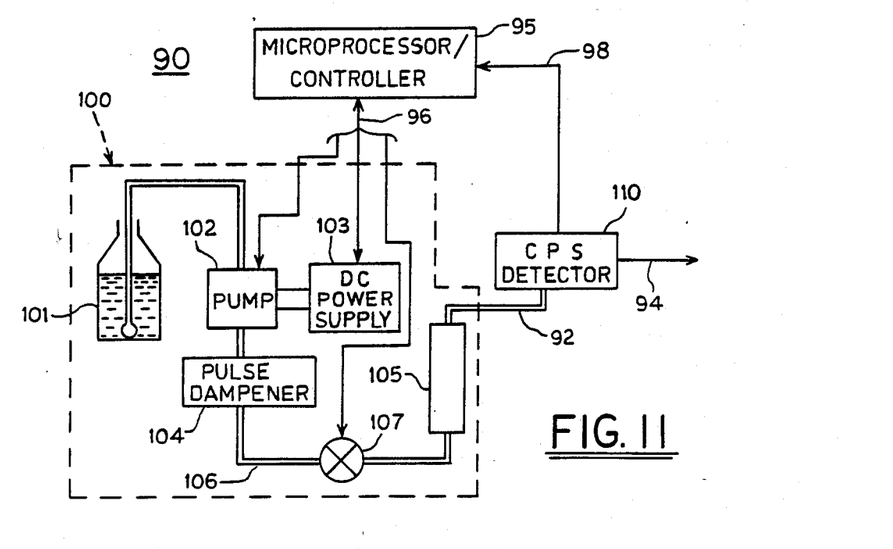
FIG. 11 is another block diagram of the system of FIG. 9, including a more detailed block diagram of the liquid chromatograph.

Referring now to FIGS. 9–11, the system 90 includes a liquid chromatographic analyzer 100, the details of which are illustrated in FIG. 11, and a CPS detector 110, the details of which are illustrated in FIG. 10, respectively connected to the microprocessor/controller 95 by cables 96 and 98. The liquid chromatographic analyzer 100 includes a mobile phase reservoir 101 from which the mobile phase is pumped by a DC pump 102 powered by a suitable DC power supply 103. Alternatively, pump 102 may be of the syringe type, powered by compressed gas from a pressurized cylinder or lecture bottle (not shown). The mobile phase is pumped through a pulse dampener 104 to the inlet end of a chromatographic column 105 via a conduit 106 and a sample injection valve 107 at which the sample to be analyzed is injected into the mobile phase stream. The outlet of the chromatographic column 105 is coupled to the CPS detector 110 via the conduit 92, the waste materials exiting the CPS detector 110 via the waste conduit 94. The cable 96 connects the microprocessor/controller 95 to the pump 102, the DC power supply 103 and the sample injection valve 107 for controlling the operation thereof.

It is a significant aspect of the invention that the liquid chromatographic analyzer 100 is a portable, low power device. Thus, the components are small and compact and are arranged to minimize the dead volume of the system. More particularly, the chromatographic column 105 is preferably a relatively small column, less than 10 cm. in length, and designed to operate at back pressures less than 150 psi, as opposed to the operating pressures for typical analytical instruments in the range from about 250 to about 2000 psi. Because of the low operating pressure of the system, the pump 102 may be a low-capacity pump consuming little power, the system preferably being designed to draw an average of less than 2 amps from the DC power supply 103. Furthermore, because of the low operating pressures, the conduits 92 and 106 carrying the mobile phase may be of relatively inexpensive, small-diameter plastic tubing, such as 1/16 inch to ⅛ inch Teflon tubing, rather than the stainless steel tubing which is typically required in analytical quality chromatographic instruments.

In one example, the liquid chromatographic analyzer 100 was designed for analysis of primary aromatic amines in association with much higher concentrations of interfering compounds, such as azaarenes, phenols and neutral aromatic hydrocarbons. The pump 102 was a 12 VDC, 60-100 ma pump of the type sold by Fluid Metering, Inc., under Model No. RP-BG25. The pulse dampener 104 was of the type with a built-in pressure gauge sold by Fluid Metering, Inc., under Model No. PD-60-LF. The sample injection valve 107 comprised an automatic sample injector containing a 20 microliter sample loop, of the type sold by Rheodyne, Inc., under Model No. 7126. The chromatographic column 105 was a 3 cm×4.6 mm $C_{18}$ (10 micrometer) reverse-phase cartridge of the type made by Brownlee Laboratories, Inc. The pump was operated by a 6 VDC battery or other suitable DC power supply, such as a 12.3 volt, 5 amp supply of the type made by Elpac Power Systems, in conjunction with a suitable variable autotransformer, of the type sold by Energy Products Co. under type No. 3PN1010. The system had a dead volume of about ½ ml.

The mobile phase was selected to give the highest sensitivities for primary aromatic amines and the least sensitivity for phenol. Therefore, a solution of 35% by volume tetrahydrofuran and 65% by volume water buffered with 0.1 M sodium phosphate at pH 2.2 was used. Sample solutions of 5 ppm primary aromatic amines were prepared in 50% aqueous acetonitrile. Coal oil A was first dissolved in benzene (3000 ppm) and then diluted to 600 ppm by adding acetonitrile. At flow rates corresponding to pressures in the range from about 30 to about 60 psi, the liquid chromatographic analyzer 100 demonstrated an ability to detect primary aromatic amines in the range of from 3-33 ppb in the presence of much higher concentrations of interfering materials derived from coal tar.

Referring to FIG. 10, the CPS detector 110 includes an array of several groups of sensors, which may be of different types. For purposes of illustration, the detector 110 has been shown with five groups of sensors, including three groups of electrochemical sensors 115 with four sensors in each group, but it will be appreciated that any number of groups and any number of sensors in each group may be utilized, depending upon the particular application. More specifically, the detector 110 includes a group 111 of four electrochemical sensors 115, connected in series to the conduit 92 carrying the eluent from the liquid chromatographic analyzer 100. From the group 111, the eluent stream is fed through an ultraviolet-irradiated tube 112 and thence to a second group 113 of electrochemical sensors 115. The eluent stream is then fed through a group 114 of suitable fluorescence sensors, and then a luminescence generating apparatus comprising chemical injection means 116 for injecting peroxyoxalate-producing mixtures into the eluent stream, which is then fed to a group 117 of chemiluminescence sensors. The eluent stream is then passed through a reagent injection device 118 for injecting suitable chemical reagents. Alternatively, the eluent stream could be passed through selected chemical filters. The stream is then passed through a final group 119 of electrochemical sensors 115 and thence to the waste conduit 94. While the sensors are shown connected in series in each group, it will be understood that they could also be connected in parallel, as in FIG. 6.

It will be appreciated that the UV-irradiated tube 112, the chemical injection device 116, and the reagent injection device 118 or selective chemical filters constitute different types of operating condition controllers for controlling the operating conditions of the sensors. These operating condition controllers, and the groups of sensors are all connected by the cable 98 to the microprocessor/controller 95. While a number of different types of operating condition controllers and different types of sensors are illustrated in the CPS detector 110 to illustrate the various types of devices which could be used, it will be appreciated that in a particular application only certain ones of these sensors or operating condition controllers may be used.

Furthermore, in the event that detection of only electrochemically active compounds is necessary, the CPS detector 110 may not require the operating condition controllers 112, 116 and 118. However, in order to detect electrochemically inactive compounds, the operating condition controllers are necessary, these controllers acting as liquid-phase equivalents of the heated filaments utilized in the CPS detectors of FIGS. 5 and 6. Thus, ultraviolet irradiation is known to convert electrochemically inactive compounds into electrochemically detectable products which may be detected by the electrochemical sensors 115 of group 113. Additionally, irradiation may cause certain components to fluoresce, so that they can be detected by the group 114 of fluorescence sensors. The chemical injection device 116 generates chemiluminescence in certain components and may be desirable in certain applications, since it produces lower detection limits than is normally obtainable with fluorescence detection for certain carcinogenic polycyclic aromatic hydrocarbons, and without requiring the use of an ultraviolet lamp. By use of the injection device 118, a variety of chemical reagents may be injected that will convert electrochemically inert species into electrochemically detectable products, also without the need for a power-consuming radiant energy source. Alternatively, as was described above in connection with FIGS. 5 and 6, the eluent stream may be passed through a series of selective chemical filters, thereby to increase the selectivity of the electrochemical sensors 115 of the group 119.

As was explained above in connection with FIGS. 5 and 6, the operating condition controllers 112, 116 and 118 may be set at a fixed condition or, alternatively, may be varied through a number of conditions while a particular component in the eluent stream is passing therethrough, so as to provide multiple responses for each of certain ones of the sensors downstream of that operating condition controller. Thus, for example the intensity of the UV-irradiation of the tube 112 may be varied or a variety of different chemicals may be injected in the devices 116 and 118, under control of the microprocessor/controller 95. Furthermore, it will be appreciated that each of the electrochemical sensors 115 has at least one operating electrode, which is normally operated at a fixed potential. However, if desired, the operating potential may be varied during exposure to a particular component in the eluent stream to vary the response of the sensors 115.

The liquid chromatographic analyzer 100 has been found to be suitable for a portable analyzer applicable in detection and identification of the compounds of interest in trace concentration under field conditions in either liquid samples or soluble (extractable) solid samples. Since the liquid chromatographic analyzer 100 is sensitive at and even below ppb levels, a simple scheme of sample handling without preconcentration may be used. Alternatively, by utilizing a suitable gas-to-liquid adsorber or absorber, the analyzer 100 could be utilized to analyze trace levels of pollutants in air samples.

However, for analysis of gas samples, the present invention preferably provides the system 120 of FIG.

12, utilizing a gas chromatographic analyzer 130 and a CPS detector 140, both operating under the control of the microprocessor/controller 95 and being coupled thereto by cables 126 and 128, respectively. In this arrangement, a commercially available gas chromatograph may be utilized, the eluent therefrom being fed via conduit 122 to the CPS detector 140, and thence to waste conduit 124. While normally a portable gas chromatograph would have inadequate resolution for analyzing complex mixtures, the feeding of the output thereof to the CPS detector 140 vastly improves the effective resolution so as to match that available in high-powered laboratory-type gas chromatographic instruments and possibly even some gas chromatography/mass spectroscopy instruments.

Figure 13:
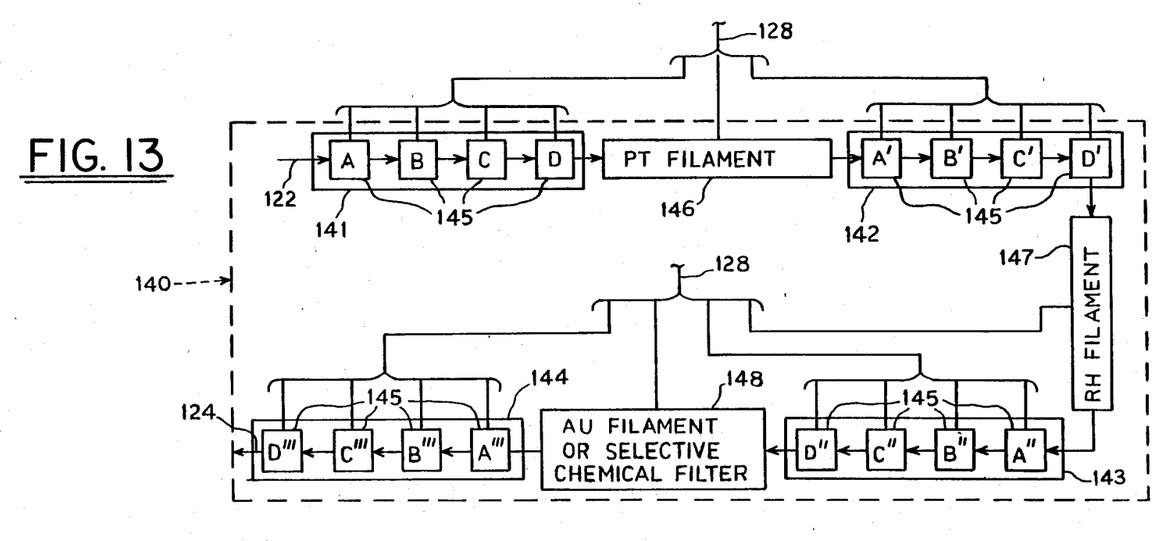
FIG. 13 is a block diagram similar to FIG. 10, illustrating the detector array utilized in the system of FIG. 12.

A CPS detector 140 which may be utilized in the system 120 is illustrated in FIG. 13, the CPS detector 140 including four groups of electrochemical sensors separated by three operating condition controllers, each group of sensors including four sensors. While this arrangement is described for purposes of illustration, it will be appreciated that, for particular applications, different numbers of groups including different numbers of sensors in each group, and different numbers and types of operating condition controllers may be utilized.

The eluent stream is applied via the conduit 122 to a first group 141 of electrochemical sensors arranged in series, and thence to a heated platinum filament 146. The eluent stream is then passed sequentially through a group 142 of the sensors 145, a Rh filament 147, a group 143 of sensors 145, a Au filament 148 or, alternatively, a group of selective chemical filters and finally a group 144 of electrochemical sensors 145. Each of the sensors 145 and filaments 146-148 are connected by the cable 128 to the microprocessor/controller 95. Thus, the temperature of the filaments 146-148 may be controlled so as to render all of the multiple sensors 145 differently selective, and also to provide detection of electrochemically inert compounds by exposing certain ones of the sensors 145 to partial oxidation or pyrolysis products generated by the heated filaments 146-148. In particular, in the CPS detector 140, the first group 141 of sensors measures the unmodified output of the gas chromatograph 130. The second group 142 of sensors measures the partly oxidized or pyrolyzed products produced by the Pt filament 146 and, similarly, the groups 143 and 144 of sensors, respectively, measure the partly oxidized or pyrolyzed products produced by the filaments 147 and 148. Alternatively, the eluent stream may be passed through a selected chemical filter, e.g., for removing a particular compound, to render the group 144 of sensors differently selective from the other groups of sensors. While the sensors in each group are arranged in series, it will be appreciated that they could also be arranged in parallel, as disclosed in FIG. 6.

As was explained in greater detail above in connection with FIGS. 1-6, it will be appreciated that each of the CPS detectors 110 and 140 produces a pattern of at least 16 different sensor outputs which can then be compared in the microprocessor/controller 95 to a library of previously established patterns to permit resolution of each chromatographic peak comparable to that achieved by some mass spectrometers.

The CPS detector works well for detecting, identifying and monitoring any one of 20-30 compounds in air at concentrations in the ppm range. However, even with groups of fewer than 20 compounds, the CPS detector could occasionally yield a misidentification, and the frequency of false identifications may be expected to increase significantly for a single group of about 100 candidate compounds.

To avoid this problem, it is another aspect of the invention to combine the pattern-matching technique of the CPS detector with a preliminary branching algorithm to extend the capability of the CPS detector to identification of any one of up to 100 different compounds. In the branching technique, a given set of about 100 compounds is divided into smaller subsets of 10-30 compounds, according to initial sensor responses, generation of negative (electro-reducing) signals in any of the different sensing modes, and rates of decay of sensor signals after discontinuance of a tested compound. These spectral features are used to first assign an unknown compound to an appropriate subset and thereafter to identify it by the pattern-matching technique. The branching greatly reduces the computation time and ensures that an increase in the number of candidate compounds will not result in a high probability of misidentifications.

The simplest type of branching would consist of grouping different compounds according to the type of sensor response that each elicits in a given operational mode or data channel. Thus, given three possible distinct types of data—positive, negative, or null—in each of P different data channels, it can be shown that the maximum number of identifiable single compounds is $3^P - 1$. It would thus appear possible to identify any one of about 100 different compounds with P greater than or equal to 5, i.e., with only five independent parameters. However, many compounds tend to share the same channels and can therefore not be distinguished from each other by a simple branching approach. Furthermore, some random spikes or drifts in background current might be mistaken for signals or, conversely, low-level signals might be mistaken for noise or drift, thereby introducing additional pitfalls. This is why it has been necessary to resort to pattern matching for identification of different compounds.

The branching approach can be best explained with reference to FIG. 14, which shows a typical sensor response curve for $NO_2$. The vertical dashed lines in FIG. 14 indicate the times of switching between different operational modes, wherein mode 0 is pure air, mode 1 is the test sample with filaments off, mode 2 is the Pt filament at 900° C., mode 3 is the Rh filament at 900° C., mode 4 is the Rh filament at 1000° C., mode 5 is the filaments off and mode 6 is pure air. The CPS detector described above uses only a minor part of the available information, viz., the net signals at the ends of modes 2, 3, 4, and 5 of FIG. 14. The signals at the ends of modes 1 and 5 are nearly identical, and the first of these is therefore typically excluded as redundant. However, this first signal provides an unambiguous distinction between electrochemically active and electrochemically inactive compounds. For electrochemically active compounds, the signal at the end of mode 1 easily exceeds 8% of the strongest signal obtained in modes 2-4, and such a significant signal can hardly be mistaken for noise or background drift. This permits a set of compounds to be divided into two major subsets.

Figure 14:
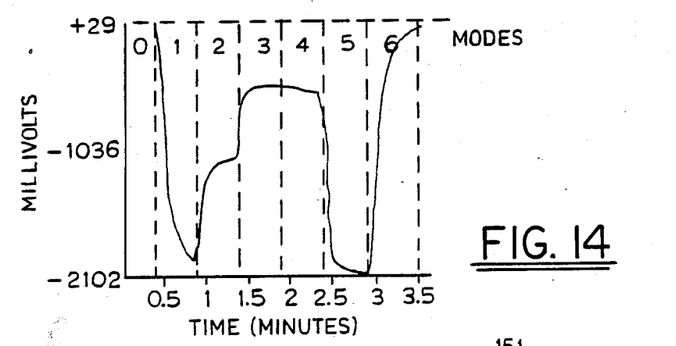
FIG. 14 is a graph showing the response pattern for $NO_2$ from a typical sensor.

Another feature found in FIG. 14 is that the signals are negative, which is characteristic of electrochemically reducible compounds. The presence of negative signals in any of the 16 channels is therefore indicative of such compounds or of electrochemically reducible products generated by a reaction at a heated filament.

This provides another simple and unambiguous criterion for dividing the above two major subsets into four smaller subsets.

In any set of compounds, a significant number may elicit their two strongest signals in the same two channels, which implies a significant probability of misidentifications when the pattern matching technique is applied to the entire set. The outlined branching yields four subsets which reduces the number of compounds sharing the same two strongest or second strongest channels and may, therefore, be expected to greatly reduce the probability of misidentifications.

But the distribution of the components is likely to be uneven, which suggests that when about 100 compounds are branched into 4 subsets, this may still yield one large subset of some 30–50 compounds. It is therefore necessary to use further branching criteria for increasing the number of separable subsets to 8 or even to 16. One such criterion may be based on the observation that, following discontinuance of certain test compounds, the signals from certain sensors may retain more than 50% of their maximum value for a period of more than 40 seconds. Compounds eliciting such a slow signal decay may therefore be branched into "sluggish" subsets. It should also be possible to achieve further branching by introducing one or more additional operational modes in which the test sample is intermittently channeled by an electronically controlled valve through a selective chemical filter (e.g., a CO-removing or $NO_2$-removing filter) before reaching the sensor array.

In performing the branching operation, the microprocessor/controller 95 performs three main subroutines: (a) a DATa IN subroutine, which reads the outputs (in microamperes), and outputs the signal-versus-time data in the form of a graph or a disk file; (b) a BRANching subROUTine, which assigns each test sample to one of 8 subsets based on the criteria of the electrochemical activity (signal magnitude at the end of mode 1 must exceed 8% of the strongest signal for the same sensor in the same test), electro-reducibility (magnitude of any negative signal greater than 60% of the strongest signal), and sluggishness of recovery (magnitude of signal at the end of the last mode must exceed 30% of that of the immediately preceding mode); and (c) an average subroutine, which uses test data obtained for known compounds and concentrations to build up a library file of the best average set of $a_{ij}$ (signal/concentration, microamperes/ppm) values for any i-th compound and j-th channel.

As test data are gathered for new compounds, they are processed by the branching algorithm, and a library is built up that stores the best average set of $a_{ij}$ values and the subset assignment for each i-th tested compound. The branching algorithm is then tested for consistency of subset assignments by treating the data from each individual test as those from an unknown sample. Any observed discrepancy is traced to its source, and appropriate corrections or adjustments are made in either the program or the experimental procedure. For instance, in borderline cases, a compound may be assigned to 2 subsets.

The branching algorithm is thereafter combined with the pattern matching algorithm, and the reliability of the identification of each compound (again treating all individual test data as those from unknown samples) is compared with that obtained by pattern matching without any preliminary branching. Also determined are be the maximum number of compounds that can be reliably identified by the branching—pattern matching combination, as well as those compounds which cannot be unambiguously identified.

Figure 15:
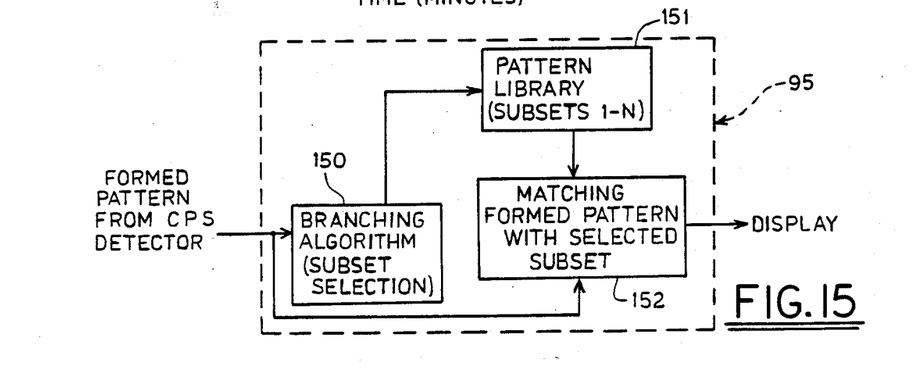
FIG. 15 is a block diagram illustrating a branching technique for use with the present invention.

Referring to FIG. 15, there is shown a simplified block diagram illustrating operation of the above-described branching technique in the microprocessor controller 95 of the present invention. The formed response pattern from the CPS detector 110 or 140 is applied to the microprocessor controller 95. It is operated on by the branching algorithm in block 150 to analyze the formed response pattern in accordance with the predetermined branching criteria and assign it to a particular subset. A subset selection signal is then applied to the pattern library 151 for selecting a predetermined subset of response patterns, which is then applied to block 152 for comparison with the formed response pattern. The identification and concentration of the component of interest is then displayed in a suitable manner. Thus, it can be seen that by the use of this branching technique the formed response pattern need only be compared with a single subset of the pattern library, thereby substantially decreasing the computation time involved and minimizing the chances of misidentifications.

As already noted, the pattern matching technique uses only a minor part of the information contained in FIG. 14. So does the branching technique described above. However, it may be possible to improve the reliability of the subset assignments and identifications by substituting the areas under the curves in FIG. 14 for the final values in each operational mode. The integrated area for each operational mode yields the time-averaged signal $I_{av}$, which is less subject to errors due to noise or transient spikes than is the instantaneous final current $I_f$ at the end of that mode. Useful information may also be derived from a comparison of $I_f$ and $I_{av}$. The $I_f/I_{av}$ ratios in certain channels can be expected to vary from compound to compound, and such variations may provide additional discrimination possibilities for improved reliability of the identifications by a CPS instrument.

From the foregoing, it can be seen that there has been provided a relatively low-cost, in-situ, real-time monitoring technique for hazardous waste materials. In particular, there has been provided a portable instrument adaptable for field or fixed-site detection and analysis of hazardous waste materials in trace amounts mixed with much larger concentrations of interfering materials.

The embodiments of the invention in which an exclusive property or privilege is claimed are defined as follows:

1. A system for analyzing a fluid sample including mixtures of components, comprising: chromatographic apparatus for achieving time-spaced separation of components of the sample, said chromatographic apparatus including a chromatographic column having an inlet and an outlet, means for introducing a carrier fluid to the inlet of said column, and means for introducing a fluid sample to the inlet of said column; detection means communicating with the outlet of said column for identifying and estimating the concentration of the components eluting from said column, said detection means including an array of sensor means, said array including plural electrochemical sensor means having differing electrochemical responses to a given one of the eluted components or to a derivative thereof dependent on the chemical interaction of the component or a derivative thereof with each of said sensor means, and non-electrochemical conditioning means downstream of said colum for operating on the component so as to selectively alter the response thereto by said electrochemical sensor means; means for arranging all of the responses of all of said sensor means in said array of sensor means into a response pattern upon exposure to the component; means for providing a plurality of previously established response patterns including a previously established response pattern for identifying the component; and means for comparing the formed response pattern with at least one previously established response pattern to identify the component.

2. The system of claim 1, wherein said chromatographic apparatus further includes electric power means and draws an average of less than two amps from said power means.

3. The system of claim 1, wherein said plurality of previously established response patterns is arranged into a plurality of subsets in accordance with predetermined characteristics of the response patterns, and further comprising means for assigning the formed response pattern to one of said subsets, said means for comparing including means for comparing said formed response pattern with only the response patterns in said one subset.

4. The system of claim 1, wherein said chromatographic apparatus is a gas chromatographic apparatus.

5. The system of claim 1, wherein said carrier fluid is a liquid and the length of said chromatographic column is less than 10 cm.

6. The system of claim 5, wherein said means for introducing the carrier fluid to the inlet of said column includes means for introducing the carrier fluid under a pressure in the range of less that 150 psi.

7. The system of claim 1, wherein said conditioning means includes a heated filament.

8. The system of claim 7, wherein said conditioning means further includes means for controlling the temperature of said heated filament.

9. The system of claim 1, wherein said conditioning means includes means for irradiating the eluent from said column with ultraviolet light.

10. The system of claim 9, wherein said array includes one or more fluorescence sensors downstream of said irradiating means.

11. The system of claim 1, wherein said chromatographic apparatus is a liquid chromatographic apparatus.

12. The system of claim 11, wherein said conditioning means includes means for injecting a peroxyoxalate-producing mixture into the eluent from said column, said array including one or more chemiluminescence sensors downstream of said injection means.

13. The system of claim 11, wherein said conditioning means includes means for injecting chemical reagents into the eluent from said column.

14. A system for analyzing a fluid sample including mixtures of components, comprising: chromatographic apparatus for achieving time-spaced separation of components of the sample, said chromatographic apparatus including a chromatographic column having an inlet and an outlet, means for introducing a carrier fluid to the inlet of said column, and means for introducing a fluid sample to the inlet of said column; detection means communicating with the outlet of said column for identifying and estimating the concentration of the components eluting from said column, said detection means including an array of sensor means, said array including a plurality of groups of sensor means and a plurality of conditioning means downstream of said column alternating with said groups to define a serial flow path through said array, each of said conditioning means operating on one or more of the components so as to selectively alter the response thereto by the sensor means downstream from said conditioning means in said flow path, at least one of said groups including plural electrochemical sensor means having differing electrochemical responses to a given one of the eluted components or to a derivative thereof dependent on the chemical interaction of the component or a derivative thereof with each of said sensor means, said conditioning means including non-electrochemical means immediately upstream of said at least one group of electrochemical sensor means; means for arranging all of the responses of all of said sensor means in said array of sensor means into a response pattern upon exposure to the component; means for providing a plurality of previously established response patterns including a previously established response pattern for identifying the component; and means for comparing the formed response pattern with at least one previously established response pattern to identify the component.

15. The system of claim 14, wherein said conditioning means includes means for passing the eluent from said column through a selective chemical filter.

16. The system of claim 14, wherein said plurality of conditioning means includes a plurality of structurally different conditioning means.

17. The system of claim 16, wherein said plurality of conditioning means includes plural heated filaments respectively formed of different noble metals.

18. A method for analyzing a fluid sample including mixtures of components, comprising the steps of: passing the fluid sample through a chromatographic column for achieving time-spaced separation of components of the sample eluting from the column, introducing the eluted components to an array of sensors including plural electrochemical sensors having differing electrochemical responses to a given one of the eluted components or to a derivative thereof dependent upon the chemical interaction of the component or a derivative thereof with each of the sensors, operating on the component by nonelectrochemical means downstream of the column so as to selectively alter the response thereto by the sensors, arranging all of the responses of all of the sensors in the array of sensors into a response pattern and comparing the formed response pattern with a set of previously established response patterns to identify the component.

19. The method of claim 18, wherein said set of previously established response patterns is arranged into a plurality of subsets in accordance with predetermined characteristics of the response patterns, and comprising the steps of assigning the formed response pattern to one of said subsets, and comparing said formed response pattern with only the response pattern in said one subset.

20. The method of claim 18, wherein the eluent from the column is passed sequentially through the sensors.

* * * * *